US009279781B2

(12) United States Patent
Wilhelm et al.

(10) Patent No.: US 9,279,781 B2
(45) Date of Patent: Mar. 8, 2016

(54) MEASURING ARRANGEMENT AND METHOD FOR REGISTERING AN ANALYTE CONCENTRATION IN A MEASURED MEDIUM

(71) Applicant: Endress + Hauser Conducta Gesellschaft für Mess- und Regeltechnik mbH + Co. KG, Gerlingen (DE)

(72) Inventors: Thomas Wilhelm, Halle (DE); Michael Hanko, Dresden (DE)

(73) Assignee: ENDRESS + HAUSER CONDUCTA GESELLSCHAFT FUR MESS- UND REGELTECHNIK MBH + CO. KG, Gerlingen (DE)

( * ) Notice: Subject to any disclaimer, the term of this patent is extended or adjusted under 35 U.S.C. 154(b) by 401 days.

(21) Appl. No.: 13/767,016

(22) Filed: Feb. 14, 2013

(65) Prior Publication Data

US 2013/0248381 A1    Sep. 26, 2013

(30) Foreign Application Priority Data

Feb. 16, 2012 (DE) .......................... 10 2012 101 254

(51) Int. Cl.
| | |
|---|---|
| *G01N 27/416* | (2006.01) |
| *G01N 27/30* | (2006.01) |
| *G01N 27/333* | (2006.01) |
| *G01N 27/49* | (2006.01) |

(52) U.S. Cl.
CPC ............ *G01N 27/30* (2013.01); *G01N 27/4167* (2013.01); *G01N 27/302* (2013.01); *G01N 27/333* (2013.01); *G01N 27/49* (2013.01)

(58) Field of Classification Search
CPC .......... G01N 27/3272; G01N 27/3277; G01N 27/302; G01N 27/333
See application file for complete search history.

(56) References Cited

U.S. PATENT DOCUMENTS

| 5,352,349 A | * | 10/1994 | Inamoto et al. ............... 205/778 |
| 6,713,308 B1 | * | 3/2004 | Lu et al. ......................... 436/514 |
| 8,562,797 B2 | | 10/2013 | McCormack |

(Continued)

FOREIGN PATENT DOCUMENTS

| CN | 101842696 A | 9/2010 |
| WO | 2005040407 A1 | 5/2005 |
| WO | 2005085825 A1 | 9/2005 |

OTHER PUBLICATIONS

Wang et al., "Iridium-Dispersed Carbon Paste Enzyme Electrodes," Electroanalysis 1996, 8, No. 5, pp. 434-437.*
Article entitled "Potentiostat Fundamentals" downloaded from the Gamry website on Oct. 20, 2015.*
Lei Fang et al, A Single-Use, Disposable Iridium-Modified Electrochemical Biosensor for Fructosyl Valine for the Glycoslated Hemoglobin Detection. In: Sensors and Actuators, vol. 137, issue 1, 2009, pp. 235-238.

(Continued)

*Primary Examiner* — Alexander Noguerola
(74) *Attorney, Agent, or Firm* — Bacon & Thomas, PLLC

(57) ABSTRACT

A measuring arrangement for registering a measured variable representing concentration of an analyte in a measured medium, includes: a first electrode modified with a redox active substance, a second electrode, and a measuring circuit, which comprises a voltage source for applying at least one predetermined voltage between the first electrode and a reference, and an apparatus for registering electrical current flowing, in such case, between the first electrode and the second electrode or for registering a variable correlated with the electrical current flowing between the first electrode and the second electrode, wherein the second electrode is modified with the same redox active substance as the first electrode.

24 Claims, 3 Drawing Sheets

(56) References Cited

U.S. PATENT DOCUMENTS

| | | |
|---|---|---|
| 8,691,073 B2 | 4/2014 | Wu |
| 2005/0270822 A1 | 12/2005 | Shrivastava |
| 2008/0110768 A1* | 5/2008 | Bae et al. .................. 205/777.5 |
| 2009/0014329 A1 | 1/2009 | Silveri |
| 2010/0032316 A1 | 2/2010 | Wu |
| 2010/0267161 A1 | 10/2010 | Wu |
| 2010/0300898 A1 | 12/2010 | Sato |
| 2011/0048969 A1 | 3/2011 | Lawrence |

OTHER PUBLICATIONS

Lei Fang et al., "An Electrochemical Biosensor of the Ketone 3-B-Hydroxybutyrate for Potential Diabetic Patient Management", In: Sensors and Actuators, vol. 129, issue 2, Feb. 22, 2008, pp. 818-825.

Richard J. Price et al., "Chemical Sensing of Amine Antioxidants in Turbine Lubricants", In: Analyst 1991, vol. 116, pp. 1121-1123.

German Search Report, Munich, Germany Dec. 10, 2012.

* cited by examiner

MEASURING ARRANGEMENT AND METHOD FOR REGISTERING AN ANALYTE CONCENTRATION IN A MEASURED MEDIUM

TECHNICAL FIELD

The invention relates to a measuring arrangement and to a method for registering a measured variable, especially an analyte concentration, an analyte activity or a pH-value, representing concentration of an analyte in a measured medium.

BACKGROUND DISCUSSION

The measuring of parameters representing concentration of an analyte in a measured medium, especially the measuring of pH-value, which reflects the concentration of $H^+$ in the measured medium, plays an important role in environmental analytics and in chemical or biochemical methods in the laboratory and in industrial process measurements technology. Analytes include, for example, certain ion types, such as $Cl^-$, $Na^+$, $NO_3^-$ or $NH_4^+$, or other substances, for example even biomolecules, dissolved in the measured medium. Electrochemical analytical methods, such as, for example, voltammetry, amperometry or potentiometry register, as a rule, the analyte activity, from which analyte concentration can be derived. In dilute solutions, to a first approximation, analyte activity can be set equal to analyte concentration.

A special case of activity, or concentration, measurement is the measuring of the pH-value. The pH-value corresponds to the negative base-10 logarithm of the $H^+$-ion activity in the measured medium, which in dilute solutions can be set equal to the $H^+$-ion concentration.

For measuring ion concentrations or pH-value both in the laboratory as well as also in process analytics, frequently potentiometric sensors are used. These include, as a rule, a measuring half-cell with an ion-selective electrode involving, for example, an ion-selective glass-, solid- or polymer membrane. The relative change of the equilibrium Galvani voltage between a measured medium and a potential sensing electrode of the measuring half-cell is, in such case, essentially effected by the activity change predominantly of the kind of ion to be determined. Referenced to a potential of a reference half-cell of essentially constant potential, e.g. a reference electrode of second type, such as the Ag/AgCl-reference electrode, the sought ion concentration or the pH-value of the measured medium can be determined by means of a high-impedance voltmeter with high accuracy and little apparatus complexity. Serving as measurement signal of such a sensor is thus the potential difference between the measuring- and reference half-cells. Ion selective electrodes are described, for example, in "Ion-Selective Electrodes", J. Koryta and K. Stulik, Cambridge University Press, 1983, Pg. 61 or in "Das Arbeiten mit ionenselektiven Elektroden (Working with Ion-Selective Electrodes)", K. Cammann, H. Galster, Springer, 1996.

The most well-known ion-selective electrode and that most frequently applied in such potentiometric sensors as a measuring half-cell is the pH-glass electrode. The glass electrode includes, as a rule, a tubular housing, which is closed on one end by a membrane of a pH-sensitive glass and which is filled with an inner electrolyte, for example, a chloride containing, buffer solution, into which a potential sensing element, for example, a chloridized silver wire, extends. In contact with the measured medium, there forms on the glass membrane a measuring half-cell potential dependent on the pH-value. Serving as a reference half-cell, as a rule, is a reference electrode of a second type, for example, a silver/silver chloride—or calomel-electrode, with a liquid junction, for example in the form of a diaphragm, between, on the one hand, a half-cell space containing the reference electrolyte and, on the other hand, the measured medium. The potential difference between the measuring half-cell potential tappable on the potential sensing element of the measuring half-cell and the reference potential of the reference half-cell (the reference potential of the reference half-cell is ideally independent of the pH-value of the measured medium) forms the measurement signal of the measuring transducer and is a direct measure for the $H^+$-ion activity, respectively the pH-value, of the measured medium.

Although such potentiometric sensors enable very precise and reliable measurement results and are well established both in the laboratory—as well as also in process analytics, they have a number of disadvantages. For example, a series of defects or degradation phenomena of the reference electrodes of the second type serving as a reference half-cell can occur to degrade the quality of the measurement. Thus, the potential of such reference half-cells tends, in practice, generally to drift, i.e. to undergo a slow, however, ongoing, change of the reference potential. Moreover, the inner electrolyte of the reference half-cell can escape or dry out. The liquid junction, via which a reference half-cell of the second type is in contact with the measured medium, can become blocked by solids, especially difficultly soluble salts, and electrode poisons can get into the reference half-cell via the liquid junction. Due to the small conductivity of the pH-sensitive glass membrane, it is additionally required to measure the potential difference between the half-cells with very high impedance, a fact which can lead to instabilities in the measuring and to measured value corruptions. Due to the high resistance of the glass of the glass membrane, limits are set on the miniaturization of such sensors. Thus, with lessening of the glass membrane area, the resistance of the measuring half-cell becomes ever greater. There is, therefore, already long the need for alternative, more robust sensor principles, which should preferably work without one of the conventional reference electrodes of second type.

Described in WO 2005/066618 A1 is a sensor for determining an analyte concentration in a measured medium in a bore hole. The sensor includes a working electrode and a counter electrode as well as an external, reference electrode. Bound on the surface of the working electrode are two or more different molecular species R and M, wherein the molecular species M is sensitive to the analyte L to be determined, for example, binds the analyte L, while the molecular species R is insensitive to the analyte L.

The analyte concentration in the measured medium can be ascertained with this sensor by registering a rectangular wave voltammogram, also referred to as a (linear) square wave voltammogram, SWV. Depending on whether the voltage between working electrode and counter electrode is increased or decreased during the registering of the voltammogram, there occurs on the working electrode an oxidation or a reduction of the molecular species R and M. These oxidation- or reduction processes show up in the plots of the electrical current flowing through the working electrode during the registering of the voltammogram as a function of the associated voltage value as (local) electrical current maxima, or (local) electrical current minima, also referred to as electrical current peaks. When, in the following, maxima, minima or extrema are discussed, unless indicated otherwise, local maxima, minima or extrema are meant.

If present on the working electrode are, respectively, a molecular species R and a molecular species M, there results, assuming that the voltage range of the voltammogram is selected appropriately broadly, respectively a first extremum associated with the molecular species R and a second extremum associated with the molecular species M. While the position of the extremum associated with the analyte sensitive species M changes as a function of the analyte concentration in the surrounding measured medium, the position of the extremum associated with the analyte-insensitive species R is independent of the analyte concentration of the measured medium. The extremum associated with the species R can, thus, serve as an additional, internal reference, so that measurement uncertainties due to degeneration effects of the external reference electrode can be recognized and/or prevented.

Similarly embodied sensors are also known from WO 2005/085825 A1 and WO 2008/154409 A1.

Disadvantageous in the case of such sensors is that the processes on the counter electrode in the described measurements are not defined. This can lead to undesired reactions with the analyte, for example, to gas evolution as a result of water decomposition. Added to this is the fact that, in the case of voltammetric measurements, frequently the oxidizing charge-flows are not equal to the reductive charge-flows on the working electrode. This means that the sensor can change in the course of its operation.

SUMMARY OF THE INVENTION

It is an object of the invention to provide a measuring arrangement, which avoids these disadvantages.

This object is achieved by a measuring arrangement for registering a measured variable representing concentration of an analyte in a measured medium, which includes a first electrode modified with a redox active substance, a second electrode and a measuring circuit, which has a voltage source for applying at least one predetermined voltage between the first electrode and a reference, as well as an apparatus for registering electrical current flowing, in such case, between the first electrode and the second electrode or for registering a variable correlated with the electrical current flowing between the first electrode and the second electrode, wherein the second electrode is modified with the same redox active substance as the first electrode.

A redox active substance in the sense of the invention is a chemical substance, which is capable of reversible release and acceptance of electrons.

Preferably, the first and second electrodes have the same area and/or the same geometric shape.

The electrodes can also be formed of the same materials. The same geometric shape of the electrodes includes that the surface regions of the electrodes in conductive contact with the measured medium during operation of the measuring arrangement have the same area within usual manufacturing tolerances.

The reference can be embodied, for example, in the form of a reference electrode in contact with the measured medium in the intended use of the measuring arrangement. In the intended use of the measuring arrangement, e.g. for performing measurements with the measuring arrangement or for regeneration of the measuring arrangement, in each case, at least one surface section of each of the first and second electrodes as well as the reference electrode is brought into contact with the measured medium, for example, by immersion. Used as reference electrode can be, for example, a drifting pseudo-reference, e.g. a metal wire, a stable potential reference electrode, e.g. an Ag/AgCl-reference electrode, or an electrode, whose potential, in a state, in which no electrical current is flowing through it, depends on the analyte concentration to be determined, as will be explained in greater detail below.

In an embodiment, an option is that the first and second electrodes do not directly contact the measured medium with a surface section, but, instead, contact an internal electrolyte accommodated in a housing and in contact with the measured medium via a liquid junction in the housing wall.

In a first additional embodiment of the measuring arrangement, there can serve as reference a reference electrode, which is embodied, especially in a state, in which no electrical current is flowing through it, to output a potential, which is independent of the concentration of the analyte in the measured medium, wherein an oxidation- and/or reduction potential of the redox active substance is influenced by the concentration of the analyte in the measured medium. Serving as reference electrode in this embodiment can be, for example, a conventional reference electrode of second type, e.g. a silver/silver chloride- or calomel electrode, as such are used in potentiometric measuring arrangements as reference half-cells. In this embodiment, the difference between the oxidation- and/or reduction potential of the redox active substance dependent on the analyte concentration and the potential of the reference electrode is a measure for the analyte concentration. The oxidation- and/or reduction potential of the redox active substance can be ascertained by measuring, for example, based on a voltammetric measurement, the electrical current flowing through the first electrode in the case of applying at least one predetermined voltage, preferably in the case of applying a voltage curve, between the first electrode and the reference electrode.

In a second additional embodiment of the measuring arrangement, an oxidation- and/or reduction potential of the redox active substance can be influenced by the concentration of the analyte in the measured medium, wherein the first and second electrodes include an additional redox active substance, whose oxidation- and/or reduction potential is not influenced by the concentration of the analyte in the measured medium. In this embodiment, the difference between the oxidation- or reduction potentials of the two redox active substances is a measure for the analyte concentration. These oxidation- and/or reduction potentials can be ascertained by measuring the electrical current flowing through the first electrode in the case of applying at least one predetermined voltage, preferably a predetermined voltage curve, between the first electrode and the reference electrode, for example, based on a voltammetric measurement. Serving as reference can be, as explained in the above described form of embodiment, a conventional reference electrode, e.g. a silver/silver chloride- or a mercury/calomel electrode, as is used also in potentiometric measuring arrangements as the reference half-cell. It is, however, also possible, to use a system internal (pseudo-) reference, for example, a metal wire.

When the analyte involves H+, the redox active substance, whose potential depends on the analyte concentration, can be selected from the group formed by anthrazenes, quinones, anthraquinones, phenanthraquinones, phenylenediamines, pyrocatechols, phenothiazines and monoquaternary N-alkyl-4,4'-bipyridine, or can comprise a substituent, which is selected from the group formed by anthrazenes, quinones, anthraquinones, phenanthraquinones, phenylenediamines, pyrocatechols, phenothiazines and monoquaternary N-alkyl-4,4'-bipyridine.

In a third additional embodiment, the redox active substance can be selected in such a manner that its oxidation- and/or reduction potential is essentially not influenced by the concentration of the analyte in the measured medium. The redox active substance can be e.g. a redox mediator. A redox mediator can reversibly, especially in a plurality of oxidation reduction cycles following one another, be oxidized by a first electrical potential and reduced by a second electrical potential.

Serving as reference in this embodiment is a reference electrode, which is embodied, especially in a state, in which no electrical current is flowing through it, to output a potential dependent on the concentration of the analyte in the measured medium. Such reference is referred to in the following also as the analyte sensitive electrode. In this embodiment, the difference between the oxidation- and/or reduction potential of the redox mediator and the potential influenced by the analyte concentration and output by the reference electrode is a measure for the analyte concentration. The oxidation- and/or reduction potential of the redox active substance can be ascertained by measuring the electrical current flowing through the first electrode in the case of applying at least one predetermined voltage, preferably in the case of applying a voltage curve, between the first electrode and the reference electrode, for example, based on a voltammetric measurement.

The reference electrode in this third additional embodiment can comprise an inner electrolyte accommodated in a housing and an analyte sensitive membrane terminating the housing in a region provided for contact with the measured medium. The terminology "analyte sensitive membrane" means, especially, a membrane, on which there arises a potential dependent on the analyte concentration in the measured medium. This potential can be tapped via a potential sensing element protruding into the internal electrolyte, for example, a metal wire, at the reference electrode in a state, in which electrical current is not flowing through it. If the analyte of concern is H+, the reference electrode used can be, for example, a glass electrode having a pH-sensitive glass membrane and a buffer solution as inner electrolyte and a potential sensing element extending thereinto.

The reference electrode can, in the third additional embodiment, equally comprise an electrolyte insulator semiconductor structure, referred to as an EIS structure, especially an ion sensitive field effect transistor (ISFET). An EIS structure comprises a semiconductor substrate on which an insulator is arranged, which in measurement operation is supplied with an electrolyte. ISFETs are established examples of sensors with an EIS structure, wherein, in this case, the insulator forms the ion sensitive gate insulator of a field effect transistor. The EIS structure or the ISFET can be embedded in a circuit, which transduces an analyte concentration dependent, primary signal produced by means of the EIS structure or the ISFET into a voltage and outputs such to the reference electrode input of the potentiostatic control circuit.

In this third additional embodiment, the redox active substance can, e.g. in the case, in which the analyte is H+, be a redox mediator, which is selected from the group formed from: Prussian, or Berlin, blue, analogs of Prussian, or Berlin, blue, derivatives of Prussian, or Berlin, blue, ferrocene, ferrocene analogs, ferrocene derivatives, ferroin, the redox system $Ce^{3+}/Ce^{4+}$ and the redox system $I^-/I_2$.

It is also possible to provide in the measuring arrangement a number of pairs of first electrodes and second electrodes, wherein, in each case, at least one such electrode pair is modified with a redox active substance, whose oxidation- and/or reduction potential is not influenced by the analyte concentration, and at least one further electrode pair is modified with a redox active substance, whose oxidation- and/or reduction potential depends on the analyte concentration. The same reference electrode can serve as reference for the two electrode pairs. Choices for this include both a reference of constant potential, as well as also a drifting, pseudo reference, e.g. a metal wire.

The redox active substance, especially the redox mediator, can, in all embodiments described here, be immobilized on electrically conductive surfaces of the first and second electrodes, for example, by binding, or bonding, it, especially covalently, to the surface of the working electrode. Alternatively, the redox active substance can be present on the surface in the form of a difficultly soluble precipitate.

The electrically conductive surfaces of the first and second electrodes can also be covered with a polymer layer, which coveres and protects the redox active substances present on the surfaces of the electrodes, especially the redox mediator. The redox active substance, especially the redox mediator, can also be bound in a polymer film, especially a conductive, polymer film, applied on the electrically conductive surfaces of the first and second electrodes.

The measuring circuit can include a control circuit, especially a potentiostatic, control circuit, which is embodied, for example, to perform amperometric and/or voltammetric measurements by means of a three electrode arrangement formed by the first electrode, the second electrode and a reference electrode serving as reference. The terminology "reference electrode" is to be understood in this connection in the sense of a potentiostatic circuit. In this sense, there can serve as reference electrode, besides a stable potential reference electrode, such as an Ag/AgCl electrode, also a pseudo-reference having a non-stable potential, e.g. a metal wire or a metal layer, or an electrode, whose potential depends on the analyte content of the measured medium.

A three electrode arrangement includes such a reference electrode, a working electrode and a counter electrode. In the example described here, for example, the first electrode forms the working electrode and the second electrode, preferably embodied with equal construction to that of the first electrode, forms the counter electrode. An example of voltammetric measurement is linear sweep voltammetry (LSV), in the case of which a direct voltage ramp is placed between the first electrode connected as working electrode and the reference electrode, i.e. in the case of which a voltage $U_{meas}$ applied between the working electrode and reference electrode (compare FIG. 1) is varied as a linear function of time. Other examples of voltammetric measurements include: staircase voltammetry, which corresponds to the LSV, wherein, however, the rise, or the fall, of the voltage $U_{meas}$ applied between the working- and reference electrodes occurs in the manner of steps as a function of time; differential pulse- or difference pulse voltammetry; and rectangular wave voltammetry, also referred to as square wave voltammetry (SWV), in the case of which there are superimposed on a direct voltage ramp, rectangular pulses with amplitude, which is smaller, especially constant, in comparison to the voltage range, over which the direct voltage ramp extends. Voltammetric measuring includes, moreover, cyclic voltammetry, also referred to as the triangular voltage method, in the case of which the voltage $U_{meas}$ applied between working- and reference electrodes is varied in a first step as a linearly rising function of time, and in a thereon following, second step as a linearly falling function of time, wherein output- and end values of the voltage $U_{meas}$ are identical in such a cycle.

The electrical current I flowing through the medium between the working electrode and the counter electrode in the case of a predetermined voltage $U_{meas}$, or in the case of a predetermined curve of the voltage $U_{meas}$, is registered as a function of time, or as a function of the voltage $U_{meas\ varying\ as\ a\ function\ of\ time}$. A plotting of the electrical current curve I as a function of the voltage $U_{meas}$ is referred to as a voltammogram, respectively a cyclic voltammogram. Details, for this, are provided, for example, in A. J. Bard, L. R. Faulkner, Electrochemical Methods, Fundamentals and Applications, John Wiley & Sons, New York, 2001, especially Chapters 6 and 7.

For performing such a voltammetric measurement, the measuring circuit can include a function generator, which is embodied to specify a voltage curve $U_{meas}$ to be applied between the first electrode, serving, for example, as working electrode, and the reference electrode, wherein the potentiostatic control circuit compensates the electrical currents flowing through the first electrode connected as working electrode via the second electrode serving as counter electrode. In this way, the reference electrode remains currentless. For example, the measuring circuit can be embodied to register the electrical current flowing through the measured medium between the working electrode and the counter electrode during the controlling to the specified voltage curve as a function of the voltage lying between the reference electrode and the working electrode. A plot of the registered electrical current as a function of the voltage is referred to as a voltammogram. The voltage curve to be established can, especially at least at times, have a linear rise, a linear fall, a step-like fall, a sawtooth curve, a triangular curve, a rectangular curve or a superpositioning of these. In a voltammetric measurement, the oxidation or reduction of a redox active substance or a redox mediator on the working electrode shows as an electrical current extremum.

The measuring arrangement can include an evaluating system, which is embodied to ascertain from an electrical current-voltage curve registered in the case of a voltammetric measurement a value of voltage lying between the working electrode and the reference electrode, in the case of which the electrical current curve has a local extremum associated with an oxidation or reduction of the redox active substance, in order, based on this value, to derive the analyte concentration in the measured medium.

If the measuring arrangement includes a function generator, then such can be a component of the evaluating system or it can be connected with the evaluating system. The evaluating system can include, for example, a data processing system with a microprocessor and at least one data memory, which the microprocessor can access. Especially, the data processing system can be a computer, for example, a PC, a measurement transmitter, a registering device or some other data processing system having an input/output interface and/or a display system, for example, a display.

In the above described, first additional embodiment of the measuring arrangement, in the case of which the redox active substance is a substance, whose oxidation- and/or reduction potential is influenced by the concentration of the analyte in the measured medium, and the reference is a reference electrode, which outputs a potential, which is independent of the concentration of the analyte in the measured medium, the value of the potential of the extremum of the voltammogram correlated with an oxidation or reduction the redox active substance correlates with the analyte concentration. From the electrical current curve of the voltammogram in the region of the extremum, the value of the oxidation-, or reduction potential of the redox active substance can be derived and therefrom, serving as a measure for the analyte concentration, the potential difference between the oxidation-, or reduction potential of the redox active substance and the potential of the reference electrode can be ascertained.

In the above described, second additional embodiment of the measuring arrangement, in the case of which the redox active substance is a substance, whose oxidation- and/or reduction potential depends on the analyte concentration, and the first electrode serving as working electrode and the second electrode serving as counter electrode include, moreover, a supplemental redox active substance, whose oxidation- and/or reduction potential is not influenced by the concentration of the analyte in the measured medium, the difference between the values of potential of the extrema of the voltammogram correlated with an oxidation or reduction of the redox active substances correlates with the analyte concentration. From the electrical current curve of the voltammogram in the region of the extrema, the oxidation-, or reduction, potentials of the two redox active substances can be derived, and therefrom, the analyte concentration ascertained.

In the above described, third additional embodiment of the measuring arrangement, in the case of which the redox active substance can be a redox mediator, whose oxidation- and/or reduction potential is essentially not influenced by the concentration of the analyte in the measured medium, and a analyte sensitive electrode is connected as reference electrode, the reference electrode yields a "reference potential" dependent on analyte concentration, i.e. the reference of the three electrode arrangement, or the position of the zero-point of the voltammogram registered by means of a voltammetric measurement, depends on the analyte concentration present in the measured medium. Since the redox mediator is insensitive relative to the analyte, the potential difference between the working- and reference electrodes, in the case of which the extremum of the electrical current associated with an oxidation or reduction of the redox mediator appears in the voltammogram, is a measure for the analyte concentration of the measured medium. From the electrical current curve of the voltammogram in the region of the extremum, the oxidation- and/or reduction potential of the redox mediator can be derived and, from the difference relative to the potential delivered by the reference electrode, the concentration of the analyte can be ascertained. In a special embodiment of the measuring arrangement, the analyte is $H^+$-ions, so that the pH-value of the measured medium can be ascertained from the position of the extremum relative to the zero-point specified by the pH-sensitive reference electrode.

In a further development of the invention, the potential curves can be monitored at the counter electrode with reference to the potential of the reference electrode and compared with the voltage curve between the working electrode and the reference electrode set by the function generator. If one of the electrodes changes or the redox active substance of these electrodes changes, the potential curves deviate from one another. The comparison can be used then to issue an error- or warning signal, which indicates need for maintenance of the measuring arrangement. The measuring circuit or an evaluating system connected with the measuring circuit can, consequently, be arranged to output an error- or warning report based on such a comparison.

The measuring circuit can be embodied in a first operating mode to connect the first electrode as working electrode and the second electrode as counter electrode and in a second operating mode to connect the first electrode as counter electrode and the second electrode as working electrode. Especially, the measuring circuit can be arranged, in a series of operating cycles following one another, wherein each operating cycle includes at least one voltammetric sweep of potential, in the case of measuring cycles following one another, in each case, to alternate the connection of the first electrode as working- or counter electrode and the second electrode as counter- or working electrode or in some other predetermined manner, so that the first electrode connected as working electrode in a first operating cycle is connected in a following, second operating cycle as counter electrode, and the second electrode connected in the first operating cycle as counter electrode is connected in the second operating cycle as working electrode. The alternation in the connection of the two electrodes modified with the same redox active substance permits at least a certain regeneration of the electrodes during operation, since the chemical reactions occurring on the electrodes in the first operating mode run in the second operating mode in the reverse direction.

A sweep of potential includes the applying of a predetermined voltage curve between the working- and the reference electrode, for example, by means of the already mentioned function generator. An operating cycle can be a measuring cycle, in the case of which measured values, e.g. in the form of a voltammogram, are registered. A operating cycle can, however, also be a pure regeneration cycle, in the case of which, indeed, a sweep of potential is performed, however, no measured values are registered and/or evaluated. The first and the following second operating cycle need not be performed directly one after the other. It is equally an option that, between operating cycles, a certain time span passes, in which the potential between working- and reference electrodes is held constant, or the measuring arrangement resides in a (turned-off), resting state. Also, an option is to perform one or more other operating cycles between the first and second operating cycles.

The first electrode and the second electrode can, in each case, have an electrically conductive, interdigital structure on at least one surface section, wherein the redox active substance is immobilized at least on this surface section of the first and second electrodes. The surface section having the interdigital structure and the redox active substance can, in an embodiment, be provided for direct contact with the measured medium.

The first electrode and the second electrode can, in another embodiment, have, in each case, an electrically conductive, interdigital structure on at least one surface section, wherein the surface sections of both electrodes extend into an inner electrolyte accommodated in a housing and the inner electrolyte is in contact with the measured medium via a liquid junction, especially via a diaphragm, wherein the redox active substance is present dissolved in the inner electrolyte or it is present as a solid. The redox active substance can supplementally be immobilized on the surface sections of the first and second electrodes having the interdigital structure. It is also an option, in an additional variation of this embodiment, that the redox active substance is immobilized on the surface sections having the interdigital structure, however, not dissolved in the inner electrolyte or dissolved in the internal electrolyte only in a small concentration determined by the solubility of the immobilized, redox active substance.

The inner electrolyte can, in an embodiment, be present as liquid, especially as an aqueous solution. Alternatively, the inner electrolyte can be present as a hydrogel. The inner electrolyte can, in an additional, alternative embodiment, comprise an ionic liquid. The redox active substance can be present dissolved in the inner electrolyte or it can be present as a solid. In a preferred embodiment, the inner electrolyte has a constant ionic strength.

The invention includes, moreover, a method for determining a measured variable representing an analyte concentration in a measured medium, wherein a first electrode serving as working electrode and modified with a redox active substance, especially a redox mediator, a second electrode serving as counter electrode, and a reference are brought into electrically conductive contact with the measured medium, wherein the second electrode is modified with the same redox active substance as the first electrode, and wherein a voltammetric measurement is performed and, based on the voltammetric measurement, the analyte concentration is ascertained.

The voltammetric measurement can be performed, for example, by means of a potentiostatic control circuit. In this connection, the reference is a reference electrode in the sense of a potentiostatic circuit, i.e. a reference, which is currentless during operation, between which reference electrode and the electrode serving as working electrode a predetermined voltage, especially a predetermined voltage curve, is placed.

As above described, for a measuring arrangement suitable for performing this method, the redox active substance can be selected in such a manner that an oxidation- and/or reduction potential of the redox active substance is influenced by the concentration of the analyte in the measured medium, wherein the reference electrode is embodied, especially in a state, in which no electrical current is flowing through it, to output a potential independent of the concentration of the analyte in the measured medium.

Alternatively, the first and second electrodes can be supplementally modified with an additional redox active substance, whose oxidation- and/or reduction potential is not influenced by the concentration of the analyte in the measured medium. Serving as reference electrode, in this case, can be a conventional reference electrode, e.g. a silver/silver chloride- or a mercury/calomel electrode. It is, however, also an option to use a system internal, reference electrode, for example, a metal wire.

Alternatively, the first and second electrodes can be modified with a redox active substance, whose oxidation- and/or reduction potential is essentially not influenced by the concentration of the analyte in the measured medium, wherein the reference electrode is embodied, especially in a state, in which no electrical current is flowing through it, to output a potential dependent on the concentration of the analyte in the measured medium. The redox active substance can be e.g. a redox mediator.

The voltammetric measurement can comprise the registering of a linear sweep voltammogram, a difference pulse voltammogram, a square wave voltammogram or a cyclic voltammogram, wherein the analyte concentration is ascertained based on at least one electrical current extremum associated with an oxidation or a reduction of the redox active substance, for example, in the manner as described above. In case the analyte involves $H^+$-ions, the pH-value of the measured medium can be derived from at least one electrical current extremum associated with an oxidation or a reduction of the redox mediator.

In an advantageous embodiment of the method, a plurality of operating cycles, e.g. measuring- or regeneration cycles, which comprise, respectively, at least one voltammetric sweep of potential, are performed sequentially, wherein the first electrode connected in a first operating cycle as working electrode is connected in a following operating cycle as counter electrode, and the second electrode connected in the first operating cycle as counter electrode is connected in a following operating cycle as working electrode. Other advantageous features of the method have already been described above based on the description of the measuring arrangement suitable for performing such measurements with different operating cycles.

For monitoring the state of the first and second electrodes, the curves of potential on the counter electrode can be monitored and compared with the curve of potential predetermined in the case of the voltammetric measurement of a measuring circuit embodied for performing the measuring. Based on of the comparison, an error- or warning signal can be output.

The method can be performed automatically, for example, by means of the above described measuring arrangement, especially controlled by an evaluating system, which includes a data processing system, e.g. a computer or a measurement transmitter.

BRIEF DESCRIPTION OF THE DRAWINGS

The invention will now be described in greater detail based on examples of embodiments shown in the drawing, the figures of which show as follows.

DETAILED DESCRIPTION IN CONJUNCTION WITH THE DRAWINGS

Figure 1:
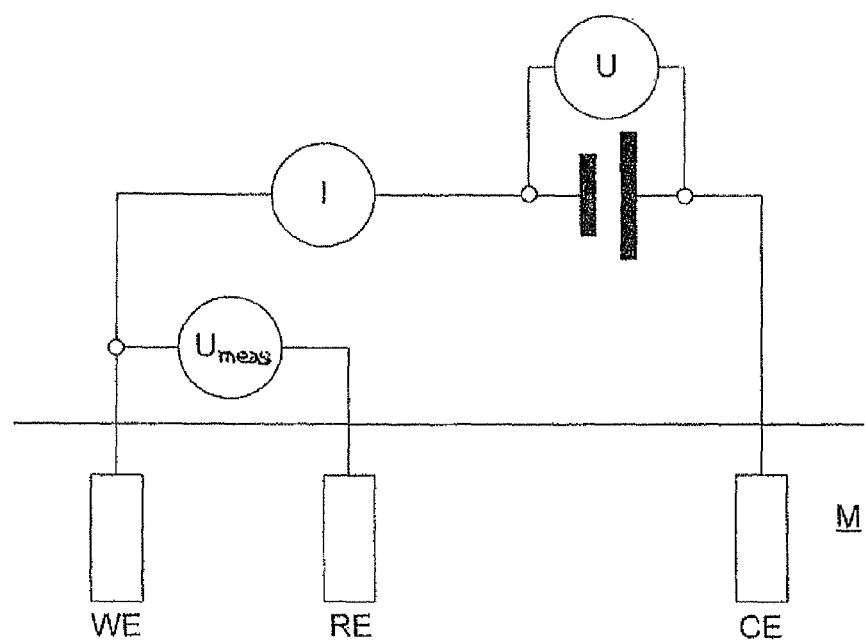
FIG. 1 is a schematic representation of a three electrode arrangement for performing a voltammetric measurement.

FIG. 1 shows schematically a three electrode arrangement 1 having a working electrode WE, a reference electrode RE and a counter electrode CE, all of which extend into a measured medium M. For performing an amperometric or voltammetric measurement, a predetermined voltage $U_{meas}$ is placed between the working electrode WE and the reference electrode RE. The predetermined voltage $U_{meas}$ can be a constant direct voltage; it can, however, also vary in time, so that a voltage curve $U_{meas}$, i.e. a voltage $U_{meas}$ variable as a function of time, lies between the working electrode WE and the reference electrode RE. The predetermined voltage curve $U_{meas}$ can be, for example, a direct voltage ramp, especially one linearly rising or linearly falling as a function of time, for registering a linear sweep voltammogram. In another example, the voltage $U_{meas}$ can also have a triangular voltage curve exhibiting a linear rise starting from a starting value and a thereon following, linear decline back to the starting value. Such a voltage curve $U_{meas}$ serves for registering a cyclic voltammogram.

The predetermined voltage $U_{meas}$ between the working electrode WE and the reference electrode RE is set, respectively controlled, based, for example, on an electrical current I flowing through the measured medium between the counter electrode CE and the working electrode WE. Control of the voltage lying between the working electrode WE and the reference electrode RE, or of the voltage curve lying between the working electrode WE and the reference electrode RE, to the predetermined voltage, or to the voltage curve $U_{meas}$, can occur by means of a potentiostat, which includes for this purpose a potentiostatic control circuit with an electronic control amplifier (not shown in FIG. 1). No electrical current flows through the reference electrode RE, in such case, so that the potential of the reference electrode RE remains uninfluenced by the control.

The potentiostat includes, furthermore, means for registering the electrical current, or the curve of the electrical current, I flowing between the working electrode WE and the counter electrode CE for bringing about the predetermined voltage, or the voltage curve, $U_{meas}$. The electrical current curve I can be expressed as a function of time and/or as a function of voltage $U_{meas}$. Such means can in the simplest case comprise an output, via which the electrical current I, or the electrical current curve I, is output in analog or digitized form to an evaluating system, for example, a data processing system, such as a measurement transmitter, a plotting device, a recording device or a computer. The potentiostat can also comprise a microprocessor and a data memory, which the microprocessor can access, and can process the registered electrical current I, or a signal derived from the electrical current I, especially a digitized and/or amplified signal, for example, by storing it in the data memory or outputting such via a display system or a communication interface.

A plot of the electrical current I flowing between the counter electrode CE and the working electrode WE as a function of the predetermined voltage $U_{meas}$ lying between the working electrode WE and the reference electrode RE, which plot is referred to here as a voltammogram, includes, consequently, electrical current extrema, which are associated with electrochemical processes occurring on the working electrode. Details for evaluation of voltammograms are set forth in the above cited text book of A. J. Bard and L. R. Faulkner.

Figure 2:
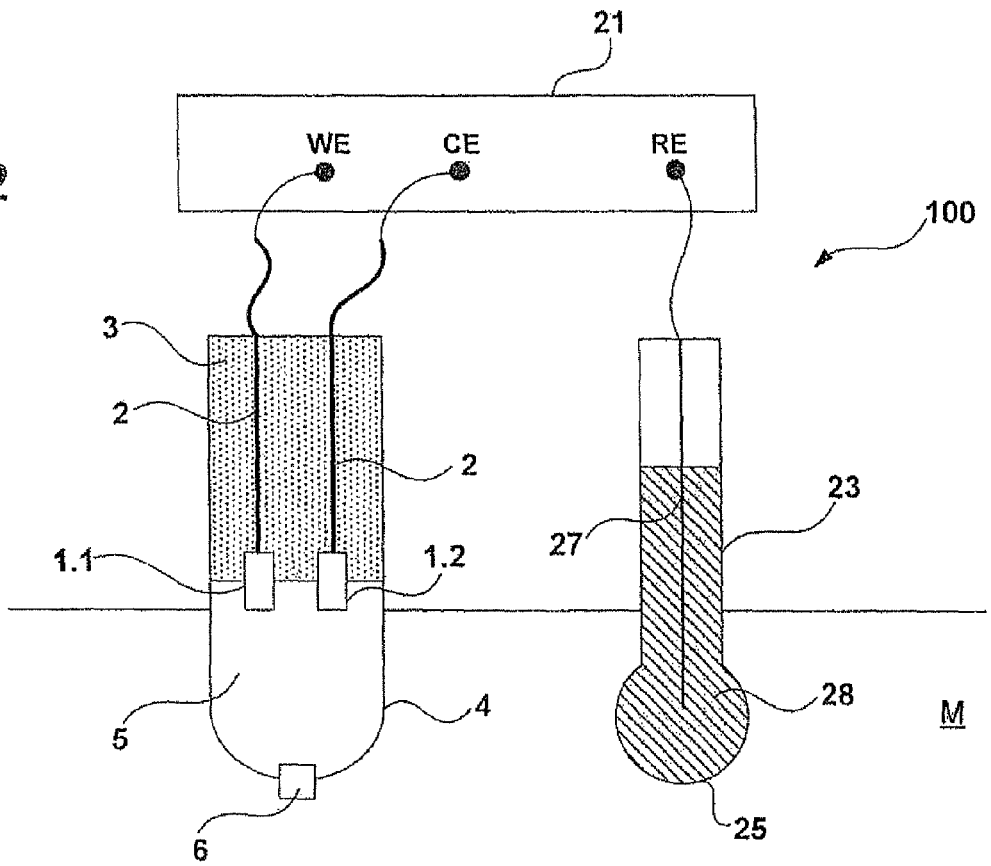
FIG. 2 is a schematic representation of a measuring arrangement for determining an analyte concentration by means of a voltammetric measurement.

FIG. 2 shows schematically a measuring arrangement 100 for performing voltammetric measurements for determining pH value in a measured medium M. In the example described here and in the following, the analyte is $H^+$-ions, so that the pH-value of the measured medium M can be derived from the voltammetric measurement. The here described measuring principle can be applied in analogous manner also for determining the concentration of some other analyte.

Measuring arrangement 100 includes two equally constructed electrodes 1.1 and 1.2. A first of these electrodes 1.1 is connected with a working electrode connection WE and the second electrode 1.2 with a counter electrode connection CE of a potentiostat 21. Both electrodes 1.1, 1.2 are accommodated in a housing 4, in which an electrolyte chamber containing an internal electrolyte 5 is formed. The inner electrolyte 5 is in electrolytic contact with the measured medium M via a diaphragm 6. The electrodes 1.1, 1.2 extend into the internal electrolyte 5 at least with a surface section provided for such purpose. The electrical contacting of the electrodes 1.1, 1.2 by the potentiostat 21 occurs by means of electrical conductors 2 led through the housing shaft 3.

Electrodes 1.1, 1.2 are of equal construction in the example shown here and both are modified by one and the same redox active substance. The surface sections of the electrodes 1.1 and 1.2 extending into the internal electrolyte and, consequently, being in contact with the measured medium M via the diaphragm 6 have essentially the same surface area. The redox active substance can, for example, be present immobilized on the surface sections of the electrodes 1.1, 1.2 extending, in each case, into the internal electrolyte 5 and/or it can be dissolved in the internal electrolyte 5. The redox active species is, in the example described here, a redox mediator, whose oxidation- and/or reduction potential is independent of the pH-value of its environment, or, in the case here, independent of the pH-value of the measured medium M.

Measuring arrangement 100 supplementally includes a reference electrode 23. In the example shown here, such is a pH-sensitive glass electrode, which outputs, in a state in which electrical current is not flowing through it, a potential dependent on the pH-value of the measured medium M. Reference electrode 23 includes a housing, which is closed on its lower end by a pH-sensitive, glass membrane 25, and in which a pH-buffer solution is accommodated as inner electrolyte 28. Extending into the inner electrolyte is a potential sensing element 27, which is connected electrically conductively with the reference electrode connection of the potentiostat 21. In contact with the measured medium M, there forms on the glass membrane 25 a potential, which depends on the pH-value of the measured medium. This potential is tapped as reference potential by the potentiostat 21.

Potentiostat 21 includes a control circuit (not shown) for setting a predetermined voltage curve between the first electrode 1.1, connected as working electrode, and the reference electrode 23, wherein the electrical currents flowing at the working electrode via the second electrode 1.2 connected as counter electrode are compensated, so that no electrical current flows through the reference electrode 23.

In contrast to conventional voltammetric measurements, in the case of which there is used as reference electrode, as a rule, a stable potential, reference electrode, e.g. an Ag/AgCl-reference electrode, the glass electrode applied here yields a reference potential dependent on the pH-value of the measured medium M.

Since the redox mediator of the working electrode 1.1 is pH-insensitive, a voltammetric measurement using a stable potential, Ag/AgCl, reference electrode in the three electrode arrangement shown in FIG. 1 would yield an electrical current extremum associated with oxidation, or reduction, of the redox mediator always at the same voltage value $U_{meas}$, independently of the pH-value of the measured medium M. Since the potential of the reference electrode RE in the example here, especially that shown in FIG. 2, does, however, vary as a function of the pH-value of the measured medium, the "zero line" of the voltammetric measurement varies correspondingly, so that also the position of the electrical current extremum associated with a reduction or oxidation of the redox mediator varies relative to this zero line as a function of the pH-value.

Figure 3A:
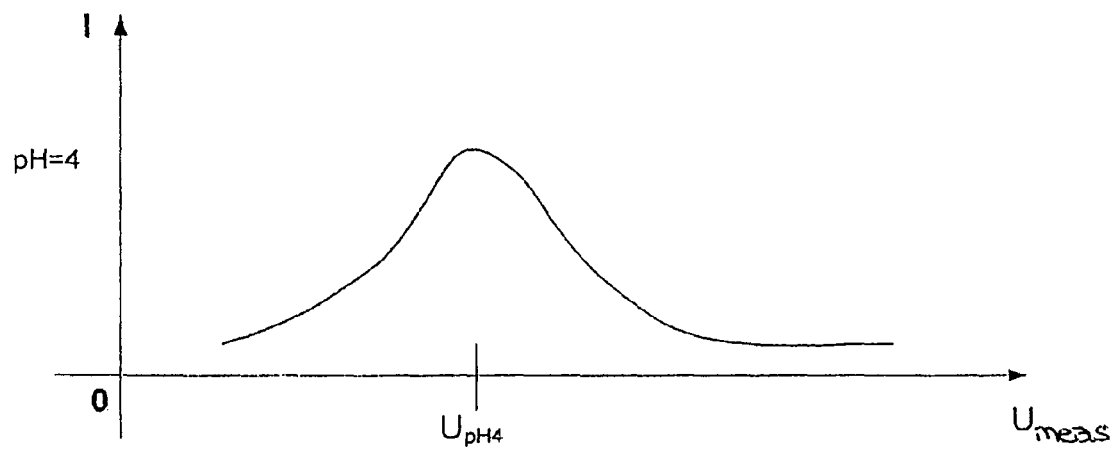
FIGS. 3A and 3B are two schematically illustrated, difference pulse voltammograms for two different pH-values.
Figure 3B:
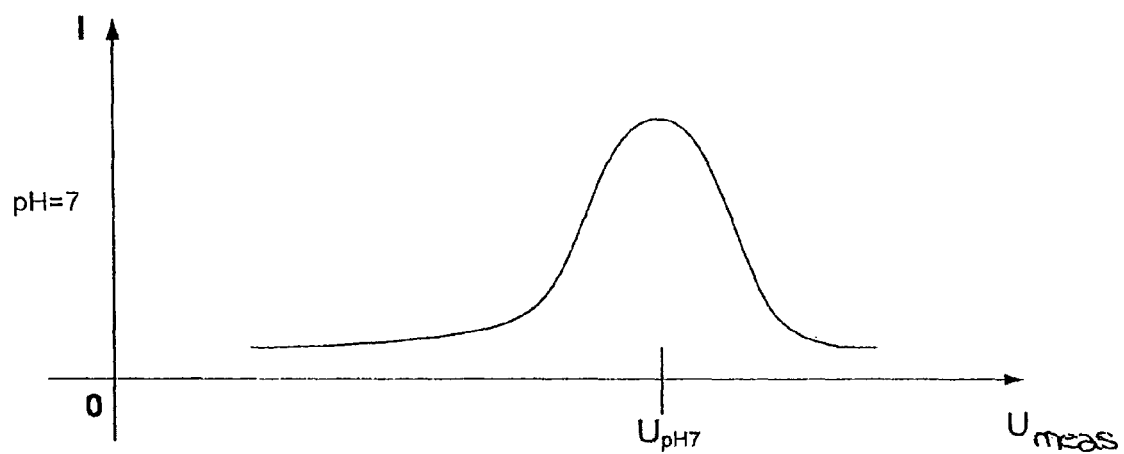

For purposes of illustration, FIGS. 3A and 3B show, schematically, two difference pulse voltammograms representing different pH-values. FIG. 3A shows a difference pulse voltammogram in the case of pH 4, and FIG. 3B in the case of pH 7. Due to the variability of the reference potential as a function of the pH-value of the measured medium M, the electrical current maximum occurring due to the oxidation of the redox mediator in the voltammogram shifts as a function of the pH-value (here to higher voltage values $U_{meas}$). The voltage values $U_{pH4}$ and $U_{pH7}$ associated with the electrical current maximum are thus a measure for the pH-value reigning in the measured medium.

Based on calibration measurements, an assignment rule can be ascertained, which permits, especially automatically, associating a pH-value with a voltage value belonging to a particular electrical current extremum. A measuring arrangement having a three electrode arrangement, a potentiostatic control circuit and an evaluating unit, which is embodied to evaluate the voltammograms registered by means of the potentiostatic control circuit as described, can, thus, based on such an assignment rule furnished in a memory of the evaluating unit, determine the pH-value of the measured medium and output and/or display corresponding measured values.

Figure 4A:
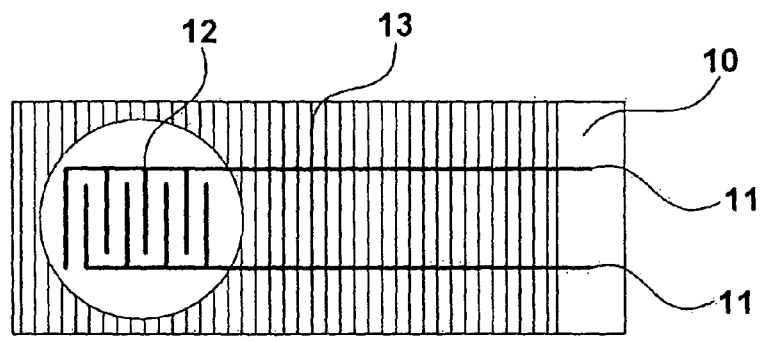
FIG. 4A shows in plan view, a schematic representation of an electrode of the measuring arrangement shown in FIG. 2.
Figure 4B:
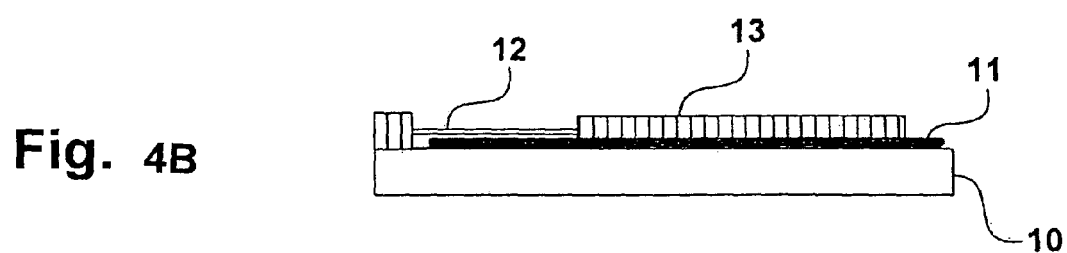
FIG. 4B shows in side view, a schematic representation of an electrode of the measuring arrangement shown in FIG. 2.

FIGS. 4A and 4B are detail views of one of the electrodes serving as working- and counter electrodes 1.1, 1.2 in the example illustrated in FIG. 2. FIG. 4A shows a plan view onto an electrode surface, while FIG. 4B shows a side view of the same electrode section. The electrode comprises a substrate 10, which can be formed of an electrically insulating material, for example, a synthetic material, e.g. a plastic, inert relative to the measured medium, a ceramic or a glass. Applied on the substrate is an electrically conductive coating 11, e.g. of a metal, such as Au, Ag, Pt, which is embodied, at least sectionally, as an interdigital structure and electrically contacted by the electrical lead 2 (FIG. 2). Applied over the electrically conductive coating 11 is an insulating layer 13, for example, an electrically insulating, polymer lacquer, which exposes a surface region 12 of the substrate surface provided with the electrically conductive coating 11. This exposed surface region 12 forms the surface region of the electrode in contact with the inner electrolyte 5 and modified by the redox mediator. The redox mediator can be immobilized in the form of a coating on this surface region. The redox mediator can be, for example, Prussian, or Berlin, blue (iron(III)-hexacyanoferrate (II/III)). The Prussian, or Berlin, blue or some other redox mediator, can be covered by a polymer layer or bound in a polymer layer. As already mentioned, it is also an option that the redox mediator is supplementally or alternatively present dissolved in the internal electrolyte 5 contained in the housing 4.

Figures 5A, 5B:
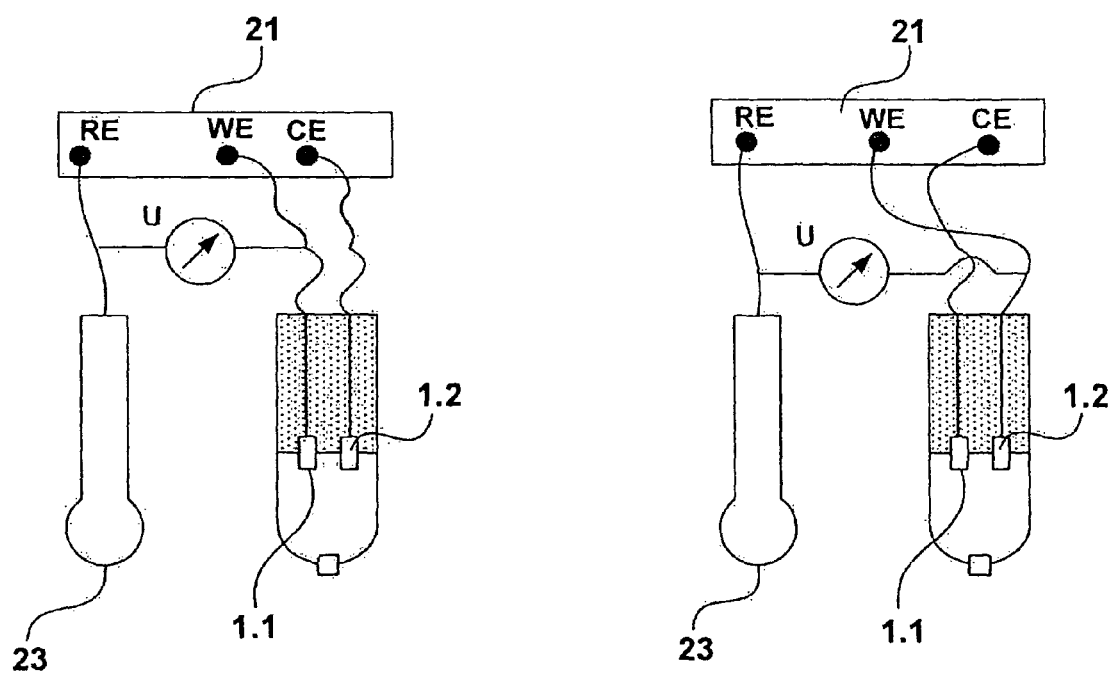
FIGS. 5A and 5B are schematic representations of first and second operating states of the measuring arrangement shown in FIG. 2.

FIGS. 5A and 5B show schematically two operating modes, in which the arrangement shown in FIG. 2 can be operated. Since the two electrodes 1.1, 1.2 are of equal construction, each of the two can, with equal result, be connected either as working electrode or counter electrode. This can be used in a method for measuring an analyte concentration, for example, a pH-value, in a measured medium to regenerate the electrodes regularly during operation. For this, in the first operating mode (FIG. 5A), the first electrode 1.1 is connected as working electrode and the second electrode 1.2 as counter electrode. In the second operating mode (FIG. 5B), the first electrode 1.1 is connected as counter electrode and the second electrode 1.2 as working electrode. When the measuring arrangement 100 is used, for example, in regular intervals, to perform measuring cycles, in order to monitor the pH-value of the measured medium M, the measuring arrangement 100 can be operated in some measuring cycles in the first operating mode according to FIG. 5A and in other measuring cycles in the second operating mode according to FIG. 5B. Advantageously, there is a regular alternation between the operating modes, e.g. in the case of sequential measuring cycles, in each case, the measuring mode can be changed over. It is also an option, to perform measuring cycles always in the first operating mode and, now and then, to perform pure regeneration cycles in the second operating mode, in the case of which only one or more sweeps of potential are executed, without the registering or evaluation of measured values.

The invention is not limited to the examples of embodiments described here. Especially, an ion-selective electrode (ISE) can be used as reference electrode in the example described based on FIGS. 2 to 5 for determining the concentration of other ions.

In another embodiment of the measuring arrangement, serving as reference can be a reference electrode, which is embodied, especially in a state, in which no electrical current is flowing through it, to output a potential, which is independent of the concentration of the analyte in the measured medium, wherein an oxidation- and/or reduction potential of the redox active substance is influenced by the concentration of the analyte in the measured medium. Serving as reference electrode in this embodiment can be, for example, a conventional silver/silver chloride- or mercury/calomel electrode. In this embodiment, the difference between the oxidation- and/or reduction potential of the redox active substance (which potential is dependent on the analyte concentration and ascertainable from the voltammetric measurement) and the potential of the reference electrode is a measure for the analyte concentration.

In an additional embodiment of the measuring arrangement, an oxidation- and/or reduction potential of the redox active substance can be influenced by the concentration of the analyte in the measured medium, wherein the first and second electrodes include an additional redox active substance, whose oxidation- and/or reduction potential is not influenced by the concentration of the analyte in the measured medium. In this embodiment, the difference between the oxidation- or reduction potentials of the two redox active substances (which potentials are ascertainable from the voltammetric measurement) is a measure for the analyte concentration. Serving as reference, as in the above described form of embodiment, can be a conventional reference electrode, e.g. a silver/silver chloride- or a mercury/calomel electrode. It is, however, also an option to use a system internal reference, for example, a metal wire.

In all these embodiments, an electrode arrangement with two electrodes modified with the same redox active species can advantageously be used. These electrodes serve, as in the example of an embodiment described based on FIG. 2, as working- and counter electrodes in a three electrode circuit embodied for performing voltammetric measurements.

The invention claimed is:

1. A measuring arrangement for registering a measured variable representing concentration of an analyte in a measured medium, comprising:
    a first electrode modified with a redox active substance;
    a second electrode; and
    a measuring circuit, which comprises a voltage source for applying at least one predetermined voltage between said first electrode and a reference electrode, as well as an apparatus for registering electrical current flowing, in such case, between said first electrode and said second electrode or for registering a variable correlated with the electrical current flowing between said first electrode and said second electrode, wherein:
    said second electrode is modified with the same redox active substance as said first electrode,
    said measuring circuit comprises a potentiostatic control circuit, which is embodied to perform measurements by means of a three electrode arrangement formed by said first electrode, said second electrode and said reference electrode,
    said measuring circuit is embodied in a first operating mode to connect said first electrode as a working electrode and said second electrode as a counter electrode and in a second operating mode to connect said first electrode as counter electrode and said second electrode as a working electrode of said three electrode arrangement.

2. The measuring arrangement as claimed in claim 1, wherein:
    said first electrode and said second electrode have same area and/or same geometric shape.

3. The measuring arrangement as claimed in claim 1, wherein:
    said reference electrode is embodied to output a potential, which is independent of the concentration of the analyte in the measured medium; and
    an oxidation- and/or reduction potential of the redox active substance is influenced by the concentration of the analyte in the measured medium.

4. The measuring arrangement as claimed in claim 3, wherein:
    the analyte is $H^+$ and the redox active substance is selected from the group consisting of anthrazenes, quinones, anthraquinones, phenanthraquinones, phenylenediamines, pyrocatechols, phenothiazines and monoquaternary N-alkyl-4,4'-bipyridine, or includes a substituent, which is selected from the group consisting of anthrazenes, quinones, anthraquinones, phenanthraquinones, phenylenediamines, pyrocatechols, phenothiazines and monoquaternary N-alkyl-4,4'-bipyridine.

5. The measuring arrangement as claimed in claim 1, wherein:
    said reference electrode is embodied to output a potential dependent on the concentration of the analyte in the measured medium; and
    an oxidation- and/or reduction potential of the redox active substance is essentially not influenced by the concentration of the analyte in the measured medium.

6. The measuring arrangement as claimed in claim 5, wherein:
    said reference electrode comprises an inner electrolyte accommodated in a housing and an analyte sensitive membrane terminating said housing in a region provided for contact with the measured medium.

7. The measuring arrangement as claimed in claim 5, wherein:
    the redox active substance is a redox mediator, which is selected from the group consisting of: Prussian, or Berlin, blue, analogs of Prussian, or Berlin, blue, derivatives of Prussian, or Berlin, blue, ferrocene, ferrocene analogs, ferrocene derivatives, ferroin, the redox system $Ce^{3+}/Ce^{4+}$ and the redox system 1112.

8. The measuring arrangement as claimed in claim 1, wherein:
    said reference electrode comprises an EIS structure.

9. The measuring arrangement as claimed in claim 1, wherein:
    said potentiostatic control circuit is embodied to perform, amperometric and/or voltammetric measurements by means of a said three electrode arrangement formed by said first electrode, said second electrode and said reference electrode.

10. The measuring arrangement as claimed in claim 1, further comprising:
    an evaluating system, which is embodied to ascertain from an electrical current-voltage curve registered in the course of a voltammetric measurement a value of voltage between said working electrode and said reference electrode, corresponding to a local extremum of the electrical current-voltage curve associated with an oxidation or reduction of the redox active substance, in order, based on this value, to derive the analyte concentration in the measured medium.

11. The measuring arrangement as claimed in claim 1, wherein:
    said first electrode and said second electrode have, in each case, on at least one surface section an electrically conductive coating; and
    the redox active substance is immobilized at least on this surface section of said first and said second electrodes.

12. The measuring arrangement as claimed in claim 11, wherein:
    said electrically conductive coating is formed as an interdigital structure.

13. The measuring arrangement as claimed in claim 1, wherein:

said first electrode and said second electrode have, in each case, on at least one surface section an electrically conductive coating;

the surface sections of both said electrodes extend into an inner electrolyte accommodated in a housing and the inner electrolyte is in contact with the measured medium via a liquid junction, especially via a diaphragm, wherein the redox active substance is present dissolved in the inner electrolyte or as a solid.

14. The measuring arrangement as claimed in claim 13, wherein:
said electrically conductive coating is formed as an interdigital structure.

15. The measuring arrangement as claimed in claim 1, wherein:
said reference electrode comprises an ISFET.

16. A method for determining a measured variable representing an analyte concentration in a measured medium, comprising:
bringing a three-electrode arrangement with a first electrode, a second electrode and a reference electrode into electrically conductive contact with the measured medium, wherein
said first electrode serves as a working electrode and is modified with a redox active substance, especially a redox mediator and
said second electrode serves as a counter electrode, and is modified with the same redox active substance as the first electrode; and
performing a voltammetric measurement using said three electrode arrangement and,
ascertaining said measured variable representing the analyte concentration on the voltammetric measurement;
performing sequentially a plurality of operating cycles, which comprise, respectively, at least one voltammetric sweep of potential; and
connecting the first electrode in a first operating cycle as a working electrode and in a following, second operating cycle as a counter electrode and connecting the second electrode in the first operating cycle as a counter electrode and in the second operating cycle as a working electrode.

17. The method as claimed in claim 16, wherein:
the first and second electrodes have same area and/or same geometry.

18. The method as claimed in claim 16, wherein:
an oxidation- and/or reduction potential of the redox active substance is influenced by the concentration of the analyte in the measured medium; and
the reference electrode is embodied, to output a potential independent of the concentration of the analyte in the measured medium.

19. The method as claimed in claim 16, wherein:
an oxidation- and/or reduction potential of the redox active substance is essentially not influenced by the concentration of the analyte in the measured medium; and
the reference electrode comprises an EIS structure, which is embodied, to output a potential dependent on the concentration of the analyte in the measured medium.

20. The method as claimed in claim 16, wherein at least one of said operating cycles is a measuring cycle, in the course of which measured values for ascertaining said measured variable are registered.

21. The method as claimed in claim 16, wherein both the first operating cycle and the second operating cycle are a measuring cycle, in the course of which measured values for ascertaining said measured variable are registered.

22. The method as claimed in claim 16, wherein at least one of said operating cycles is a regeneration cycle, in the case of which a sweep of potential is performed, but no measured values are registered.

23. The measuring arrangement as claimed in claim 16, wherein said redox active substance is a redox mediator.

24. A measuring arrangement for registering a measured variable representing concentration of an analyte in a measured medium, comprising:
a first electrode modified with a redoxly redox active substance;
a second electrode; and
a measuring circuit, which comprises a voltage source for applying at least one predetermined voltage between said first electrode and a reference electrode, as well as an apparatus for registering electrical current flowing, in such case, between said first electrode and said second electrode or for registering a variable correlated with the electrical current flowing between said first electrode and said second electrode, wherein:
said second electrode is modified with the same redox active substance as said first electrode said measuring circuit comprises a control circuit, which is embodied to perform amperometric and/or voltammetric measurements by means of a three electrode arrangement formed by said first electrode, said second electrode and said reference electrode,
said measuring circuit is embodied in a first operating mode to connect said first electrode as a working electrode and said second electrode as a counter electrode and in a second operating mode to connect said first electrode as counter electrode and said second electrode as a working electrode.

* * * * *